United States Patent [19]
Bowen

[11] Patent Number: 4,734,560
[45] Date of Patent: Mar. 29, 1988

[54] VAPORIZING UNIT

[75] Inventor: John G. Bowen, Fordingbridge, England

[73] Assignee: Medical Enterprises, Ltd., Guernsey, Channel Islands

[21] Appl. No.: 5,146

[22] Filed: Jan. 20, 1987

[51] Int. Cl.⁴ .......................... A61L 9/03; H05B 3/14
[52] U.S. Cl. .................................. 219/271; 219/274; 219/275
[58] Field of Search ............... 219/271, 272, 273, 274, 219/275, 276, 439; 422/125, 305, 306

[56] References Cited

U.S. PATENT DOCUMENTS

| | | | |
|---|---|---|---|
| 2,513,919 | 7/1950 | Costello | 219/272 |
| 2,931,880 | 4/1960 | Yaffe | 219/271 |
| 3,764,780 | 10/1973 | Ellis | 219/439 |
| 3,998,590 | 12/1976 | Glorieux | 219/439 |
| 4,270,039 | 5/1981 | Hauser | 219/439 |
| 4,391,781 | 7/1983 | van Lit | 219/274 |
| 4,529,868 | 7/1985 | Bowen | 219/439 |
| 4,588,874 | 5/1986 | Napierski | 219/271 |

FOREIGN PATENT DOCUMENTS 55-23853  2/1980  Japan ................................. 219/274

*Primary Examiner*—E. A. Goldberg
*Assistant Examiner*—Teresa J. Walberg
*Attorney, Agent, or Firm*—Keith D. Beecher

[57] ABSTRACT

An electrically energized vaporizing unit for medications, room deodorizers, room scenting compounds, room insecticides, and the like, is provided which is simple and inexpensive in its construction and which is compact in size. The vaporizing unit has one or more compartments which are adapted to be filled with a liquid to be vaporized, or to hold a solid tablet saturated with a substance to be vaporized, the compartments being heated by positive thermal coefficient (PTC) electrical heating elements in conjunction with paraffin wax, the melting point of the wax being selected to correspond to the vaporizing temperature of the particular substance in the compartments. The vaporizing unit is equipped with an electric plug which may be directly plugged into an electric receptacle to energize the PTC heating elements, and it does not require a switch or protective thermostats.

4 Claims, 8 Drawing Figures

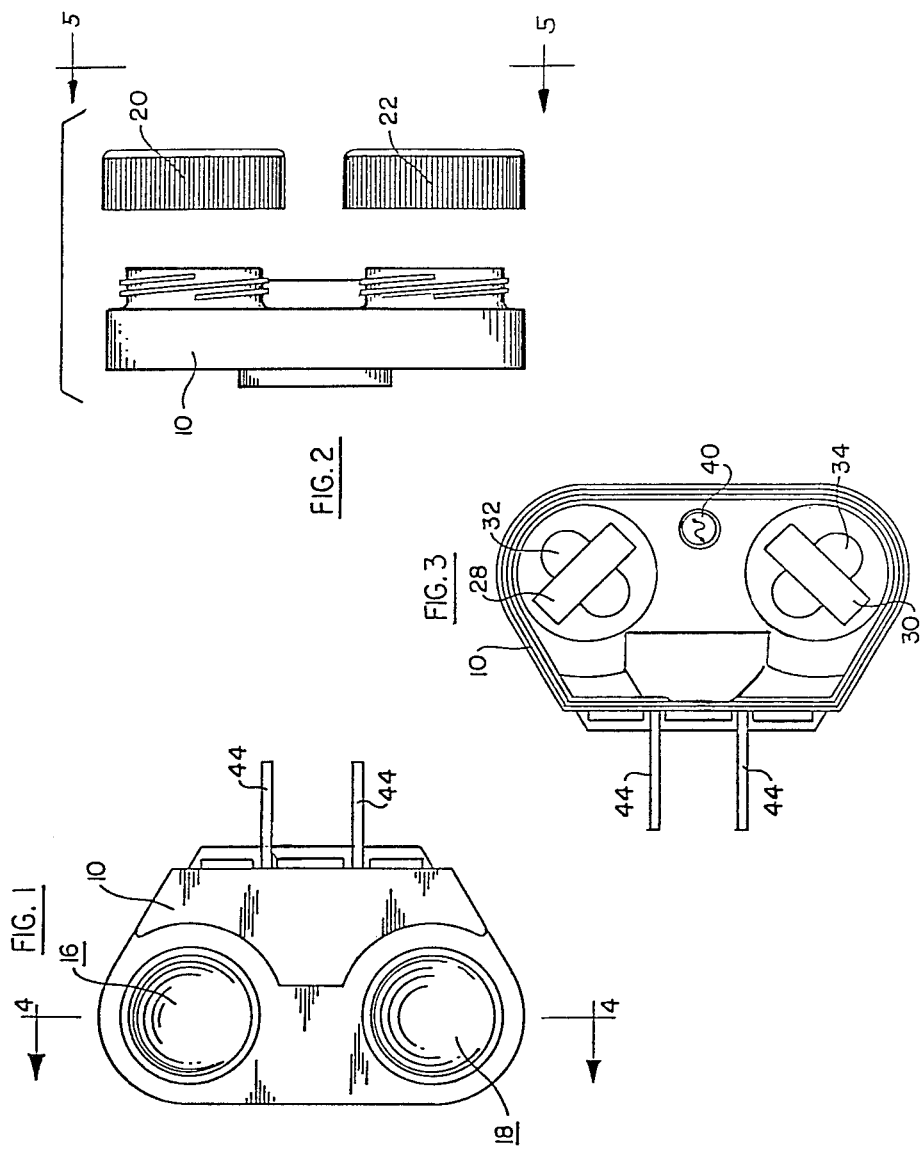

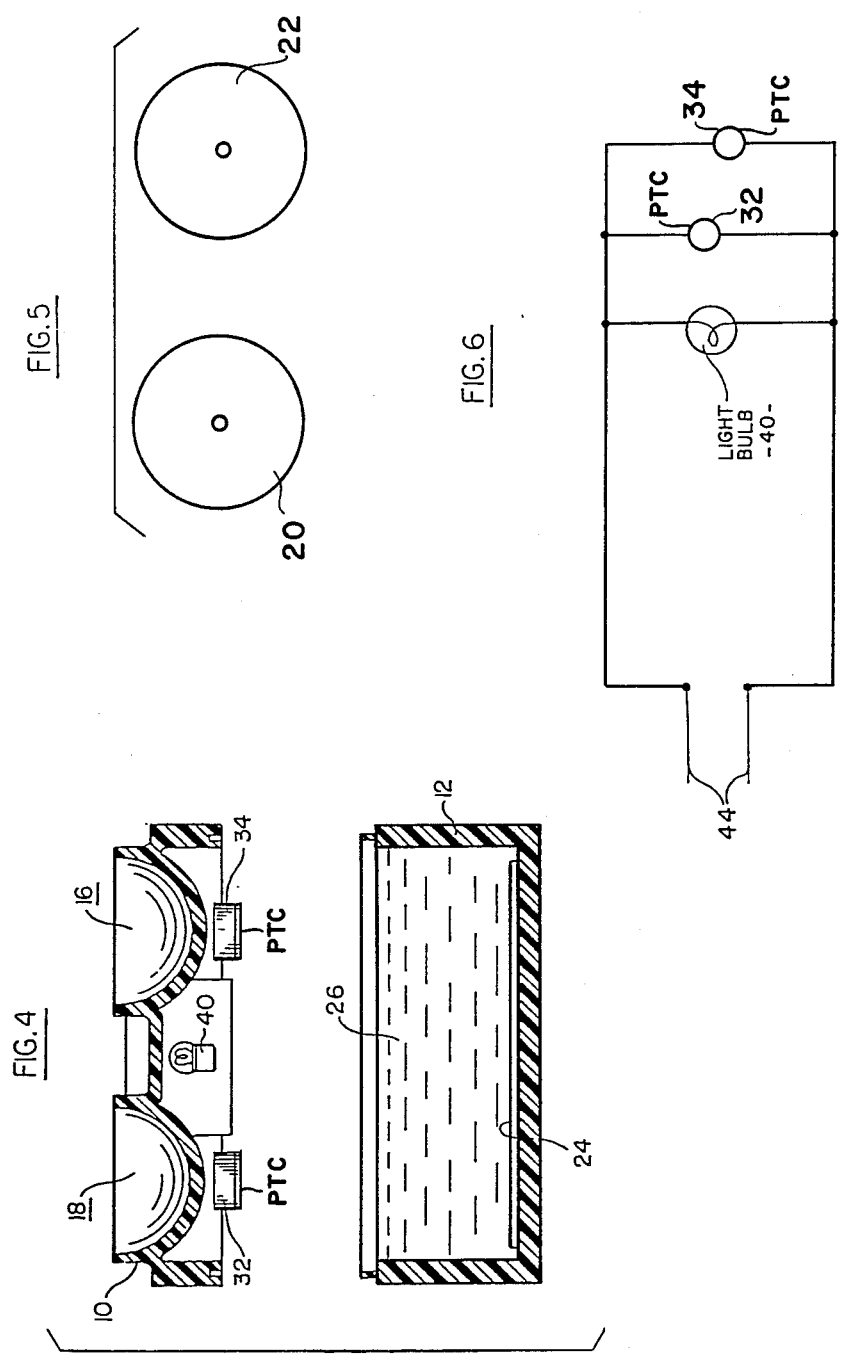

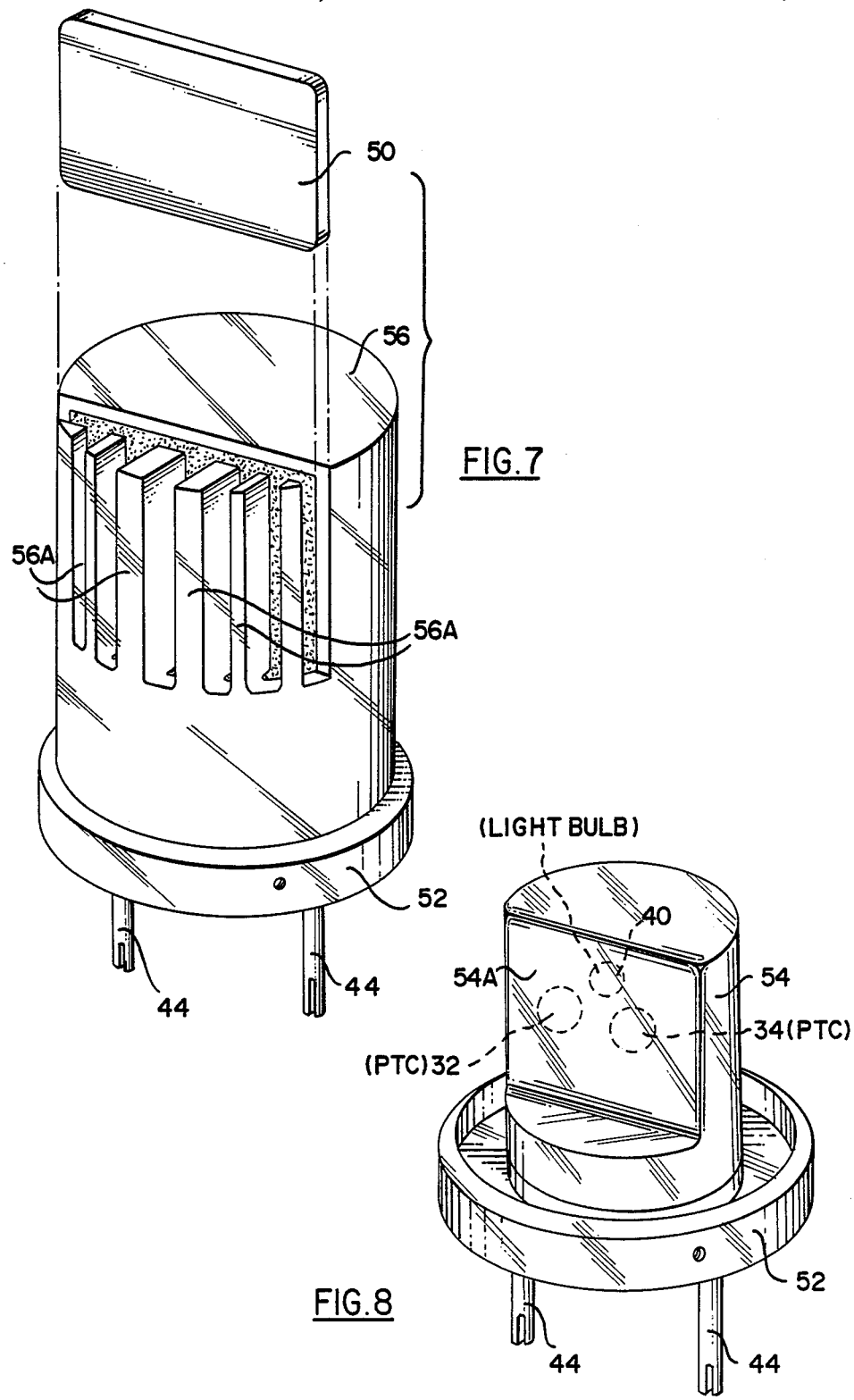

VAPORIZING UNIT

BACKGROUND OF THE INVENTION

The vaporizing unit of the present invention is similar in some structural respects to the soft contact lens disinfecting unit described in application Ser. No. 317,071 which was filed Nov. 2, 1981 in the name of the present inventor and Stephen G. Hauser, and which issued July 16, 1985 as U.S. Pat. No. 4,529,868.

The prior art vaporizers, for the most part, use steam to vaporize a medication or other substance, so that the medication may be raised to a constant vaporizing temperature and vaporized at that temperature over a relatively long period of time. The vaporizer of the present invention, on the other hand, provides a dry vaporizing action by which a medication, or other substance to be vaporized, is vaporized directly at its vaporizing temperature for substantially long periods of time, without any need for the generation of steam.

The vaporization unit of the invention, like the unit described in U.S. Pat. No. 4,529,868, and like the unit described in U.S. Pat. No. 4,158,126, uses a paraffin wax, or equivalent material, to transmit the heat from the heating elements to the heating wells, or to a solid tablet, so that a predetermined temperature may be established in the heating wells, or at the tablet, which remains constant over prolonged periods of time.

SUMMARY OF THE INVENTION

An electrically energized vaporizing unit in which the substance to be vaporized is heated by positive thermal coefficient (PTC) electrical heating elements in conjunction with paraffin wax. The melting point of the wax is selected to match the vaporizing temperature of the substance. This enables the temperature of the substance to be raised to its vaporizing temperature and held at that temperature over long periods of time. The unit may be used for medication purposes, or for room scenting or deodorizing, or the like. In addition, the unit may be used for vaporizing an insecticide into a room.

BRIEF DESCRIPTION OF THE DRAWINGS

FIG. 1 is a top plan view of the upper housing of a unit constructed in accordance with a first embodiment of the invention which includes wells for holding a liquid to be vaporized, with the covers of the unit removed;

FIG. 2 is a side view of the upper housing of the unit of FIG. 1, showing the covers displaced from the top of the upper housing;

FIG. 3 is a bottom view of the upper housing of the unit of FIG. 1 revealing the components mounted within the upper housing;

FIG. 4 is a section of the upper housing taken along the line 4—4 of FIG. 1, and also a section of the lower housing shown displaced from the upper housing;

FIG. 5 is a top plan view of the covers of the unit taken along the line 5—5 of FIG. 4;

FIG. 6 is a circuit diagram showing the connections to the various electrical elements within the unit;

FIG. 7 is a perspective view of a second embodiment of the invention which is constructed to hold a solid tablet impregnated with a substance to be vaporized; and FIG. 8 is a perspective view of the unit of FIG. 7 with its cover removed.

DETAILED DESCRIPTION OF THE ILLUSTRATED EMBODIMENTS

The vaporizing unit illustrated in FIGS. 1-6 of the drawings includes an upper housing 10 formed of any appropriate plastic material, and a lower housing 12 (FIG. 4) which preferably is formed of a transparent plastic material. The upper housing is configured to define a pair of adjacent wells 16 and 18, each of which is intended to be filled with a liquid to be vaporized. It is evident that one well may be used if so desired. When the wells are filled with the particular liquid, covers 20 and 22 (FIGS. 2 and 5) are screwed down over the top of the wells. Each of the covers has a central orifice which allows vapor to escape from the wells when the unit is energized, as best shown in FIG. 5. The diameters of the central orifices are adjusted to a predetermined desired vaporization rate.

The upper housing 10 is fitted down over the lower housing 12, and the two housings are bonded together. A red indicator sheet 24 is affixed to the bottom of the lower housing (FIG. 4), and the lower housing is filled with an appropriate fluid, such as paraffin wax 26. In fact, the unit can be filled so that the paraffin wax not only fills the lower housing 12, but also at least partially fills the interior of the upper housing 10. The paraffin wax is selected so that its melting temperature corresponds with the vaporization temperature of the substance being vaporized in the unit.

The unit is provided with two blades 44 mounted on housing 10. These blades protrude outwardly from the housing to constitute an electric plug which may be plugged directly into an electrical receptacle.

A pair of positive thermal coefficient (PTC) heating elements 32 and 34 are mounted in the upper housing 10 under the corresponding wells 16 and 18. Each of the heating elements 32 and 34 is connected to blades 44, as shown in FIG. 6. PTC heating elements have been known for many years. These units are composed of a semiconductor ceramic, such as appropriately doped barium titanate. This material has a positive thermal coefficient, and it has a property that at a certain temperature, known as the Curie point, its internal resistance suddenly increases if temperatures are raised above that point.

Accordingly, the PTC heating element is attractive because of its automatic temperature control. The PTC heating element is independent of voltage, and can be used in conjunction with alternating current or direct current. Regardless of voltage, the element will increase in temperature until the Curie point is reached, and at that point it will effectively cut off, serving inherently as an automatic temperature controller. Moreover, the PTC heating element does not require a protective relay in its circuit, because it is incapable of burning out. These features enable the unit of the invention to be used worldwide, in conjunction with alternating current or direct current mains of a variety of voltages.

The Curie point of the PTC heating element can be set to any desired temperature level by the selection of the doping of the ceramic material. In the case of the vaporizing unit of the present invention, this level is set to correspond with the vaporizing temperature of the substance being vaporized in the unit.

It is known that the Curie point cannot be set with any degree of accuracy, and variations up to ±40% have been experienced from one PTC heating element to another. However, in the vaporizing unit of the present invention, the PTC heating elements 32 and 34 are embedded in paraffin wax, and the wax is used to carry the heat from the heating elements to the wells.

The paraffin wax is selected to have a melting point which corresponds with a high degree of accuracy with the vaporizing temperature of the particular substance to be vaporized. The Curie point of the PTC heating elements is then set to occur above the melting point of the wax, even with its widest variation. During normal operation the wax is never completely melted, and its latent heat establishes a precise vaporizing temperature for the vaporizing unit.

As mentioned above, there is no need for a cut-off relay in circuit with the PTC heating elements because, if for any reason the elements are heated above the normal operating temperature of the vaporizing unit, this being due, for example, for their coming out of contact with the wax, or for any other reason, the increased temperature never exceeds the Curie point. Thus, the heating elements 32 and 34 are capable of achieving a precise vaporizing temperature insofar as the wells of the unit are concerned.

A light bulb 40 is also mounted in the upper housing, and is connected to blades 44, as shown in FIG. 6, to be illuminated when the vaporizing unit is energized. When the wax 26 is melted, the wax becomes transparent, so that the bulb 40 causes a red glow to eminate from the bottom of the lower housing 12, due to the red indicator sheet 24, to indicate intervals when the unit is actually energized. Also, the red indicator sheet 24 is visible through the side walls of the transparent lower housing 12 when the wax is molten, to indicate that the wax is in a molten state, and the vaporizing unit is operating.

To operate the unit of FIGS. 1–5, the substance to be vaporized is placed in the wells 16 and 18, and the covers 20 and 22 are screwed down over the wells. The blades 44 of the unit are then plugged into an electric receptacle, and the heating elements 32 and 34 are energized and heat the wax 26 within the unit, to cause the wax to become partially molten. During the entire operation of the unit, the wells 16 and 18 are held at the vaporizing point of the substance being vaporized due to the latent heat of the wax 26, the wax being selected to have a latent heat corresponding to the desired vaporizing temperature. The light bulb 40 glows to show that the unit is energized, and the glow from the red indicator sheet 24 shows tht the wax is in a molten state.

The unit continues to vaporize the substance in the wells over a substantial time period, and the vapor from the substance is discharged through the orifices in the covers 20 and 22 at a predetermined rate established by the size of the orifices. If for any reason the temperature of the heating elements 32 and 34 should tend to rise above the vaporizing temperature, due to the inherent characteristics of the units, they will cut off so as to form their own protective system.

The embodiment of FIGS. 7 and 8 is intended to hold a solid tablet 50 which is impregnated with the substance to be vaporized. Tablet 50 may be of the type marketed by Fumakilla Limited of Tokyo, Japan, under the trademark "Vape Mat f".

The unit shown in FIGS. 7 and 8 includes a base 52. The blades 44 of the electric plug are mounted on the base and protrude downwardly from the bottom of the base.

An inner housing 54, preferably formed of glass, is mounted on the base 52. The PTC heating elements 32 and 34, and light bulb 40, are contained and sealed in housing 54. The heating elements are embedded in paraffin wax which is also contained in the inner housing.

Inner housing 54 has a generally hemi-cylindrical shape with a flat face 54A. The unit also includes an outer housing 56 mounted on base 52 coaxially with inner housing 54. The outer housing 56 includes a grill 56A which forms a slot for receiving tablet 50. The tablet is held by the grill against the flat face 54A of the inner housing to be heated to the vaporizing temperature of the substance with which the tablet is saturated. The resulting vapor passes through the grill 56A. The outer housing is preferably formed of nylon which does not have a tendency to discolor from dyes contained in some of the tablets 50.

Tablet 50 may be disposable or it may be recharged by an appropriate vial and syringe.

The invention provides, therefore, a safe, simple, inexpensive and compact vaporizing unit which may conveniently be plugged into a wall receptacle when in use. It will be understood, of course, that while particular embodiments of the invention have been shown and described, modifications may be made. It is intended in the claims to cover all modifications which come within the true spirit and scope of the invention.

I claim:

1. An electrically energized vaporizing unit for directly vaporizing medication substances, and the like, comprising: a bose; an inner housing having a generally hemi-cylindrical shape mounted on said base, said inner housing having a generally flat face; electrically energized PTC heating means mounted in the inner housing; electric circuitry mounted in the inner housing for connecting the heating means to a source of electric energy; a material contained in the inner housing for conducting heat from the heating means to the flat face thereof and which becomes at least partially molten after a particular time interval following the energization of the heating means; an outer housing mounted on said base coaxially with the inner housing and defining a slot adjacent to said flat face of said inner housing for receiving a vaporizing tablet and for supporting said tablet adjacent to said front face of said inner housing; and said outer housing including a grill adjacent to said tablet for passing vapor from said tablet, said material contained in said inner housing having a melting point corresponding to the vaporizing temperature of said tablet and said PTC heating means having a Curie point above the melting point of the material.

2. The electrically energized vaporizing unit define in claim 1, in which said material contained in said inner housing is paraffin wax.

3. The electrically energizing vaporizing unit defined in claim 1, and which includes an electric indicator lamp mounted in said housing and connected to said circuitry to be energized when the unit is energized.

4. The electrically energized vaporizing unit defined in claim 1, and which includes a pair of electrically conductive elongated members mounted on said housing and protruding therefrom to form an electric plug, said electric circuitry being connected to said elongated members.

* * * * *